United States Patent
Cha

(10) Patent No.: US 6,256,532 B1
(45) Date of Patent: Jul. 3, 2001

(54) APPARATUS FOR ANALYZING BODY COMPOSITION BASED ON BIOELECTRICAL IMPEDANCE ANALYSIS AND METHOD THEREOF

(75) Inventor: Ki Chul Cha, Seoul (KR)

(73) Assignee: Biospace Co., Ltd. (KR)

( * ) Notice: Subject to any disclaimer, the term of this patent is extended or adjusted under 35 U.S.C. 154(b) by 0 days.

(21) Appl. No.: 09/495,096

(22) Filed: Feb. 1, 2000

(30) Foreign Application Priority Data

Jul. 29, 1999 (KR) .................................................. 99-31019

(51) Int. Cl.⁷ ....................................................... A61B 5/05
(52) U.S. Cl. .............................................................. 600/547
(58) Field of Search ............................................. 600/547

(56) References Cited

U.S. PATENT DOCUMENTS

| | | | |
|---|---|---|---|
| 4,895,163 | 1/1990 | Libke et al. | 128/734 |
| 4,911,175 | 3/1990 | Shizgal | 128/734 |
| 5,335,667 | 8/1994 | Cha et al. | 128/734 |
| 5,415,176 | * 5/1995 | Sato et al. | 600/547 |
| 5,579,782 | * 12/1996 | Masuo | 600/547 |
| 5,720,296 | 2/1998 | Cha | 128/734 |

\* cited by examiner

Primary Examiner—Robert L. Nasser
Assistant Examiner—Pamela L. Wingood
(74) Attorney, Agent, or Firm—Woodcock Washburn Kurtz Mackiewicz & Norris

(57) ABSTRACT

The apparatus for analyzing the body composition based on the bioelectrical impedance analysis according to the present invention includes a standing plate having four electrodes for contacting a right front sole, a right rear sole, a left front sole, and a left rear sole, respectively; a hands bar having four electrodes for contacting a right palm, a right thumb, a left palm, and a left thumb, respectively; a support rod for supporting the hands bar and connecting an axis; a display; a sensor for sensing the rotating position of the support rod and indicating the height of the measuring person to the display; an impedance measuring circuit for measuring the impedance based on a voltage-current ratio by making an alternating current flow between two of the electrodes and reading the voltage difference; an electronic switch for being controlled by a microprocessor to select electrical connections between the electrodes and the impedance measuring circuit; a weight measuring sensor for measuring the body weight of the measuring person; an A/D converter and amplifiers for interfacing the impedance measuring circuit, the weight measuring sensor, and the sensor for indicating the height to the micro-processor; and the microprocessor controlling the electronic switch and processing the data received from the impedance measuring circuit, the weight measuring sensor, and the sensor for indicating the height.

11 Claims, 10 Drawing Sheets

APPARATUS FOR ANALYZING BODY COMPOSITION BASED ON BIOELECTRICAL IMPEDANCE ANALYSIS AND METHOD THEREOF

FIELD OF THE INVENTION

The present invention relates to an apparatus for analyzing conveniently body composition based on bioelectrical impedance analysis, and a method thereof. In particular, the present invention relates to an apparatus for measuring the impedance of the body segments by contacting the hands and the feet to metal electrodes and by adjusting a hands bar to the height of the measuring person so as to input the height automatically, and a method for quantitatively analyzing body composition such as body fluid, body fat, and the like. According to the present invention, the data on height, age, sex, and the like are not inputted through a keyboard.

BACKGROUND OF THE INVENTION

A human body is composed of water, protein, bone and fat, in addition to small amounts of special components. The total of these elements constitutes the body weight. Quantitatively measuring the respective elements is called body composition analysis. Recent years body composition analyzers have been actively developed due to interest in health care from fatness. The proportion occupied by the fat is called fatness and is used in diagnosing various adult diseases. In the medical terms, of the body composition, fat free mass (FFM) is the main component for supporting the human body. Patients suffering from malnutrition related, for example to cancer are subject to a periodic FFM measurement to determine a remission state or monitor progress of the disease. In the case where a fatty man performs athletic exercises to reduce the body weight, it frequently happens that the body weight shows almost no variation within a relatively short period of several months. In this case, if the body composition is measured, it will be found that the amount of muscle has increased, although the amount of fat has decreased. In this way, the effect of the athletic exercise can be measured in a rational manner. Further, based on the analysis of the body composition, the growth of children and the nutritional status of elderly men can be diagnosed. Particularly, for various patients, the segmental water distribution can be measured to determine patient's hydration status.

As one of conventional methods for measuring the body composition, bioelectrical impedance analysis (BIA) is widely employed. This method is carried out in the following manner. That is, a weak alternating electric current is passed across the human body to measure the electrical resistance or conductance of the body, as well as measuring the height and weight. Based on these measured values, the amount of the body fluid, the fluid balance inside and outside the cell, and the amount of the body fat are calculated.

FIG. 1 represents a conventional embodiment using the BIA method. According to the conventional BIA method, body composition is analyzed by a series of steps of attaching the electrodes on the hands and feet, inputting sex, age, weight, and height of the measuring person, measuring impedances at the respective body parts, calculating body compositions in a microprocessor, and displaying the resulting data on a display or printing the data out through a printer. Such conventional BIA method has disadvantages that an operator attaches the electrodes on the hands and feet of the measuring person, and that the operator or the measuring person inputs the sex, age, weight, and height of the measuring person through a keyboard.

FIG. 2 represents another embodiment using the BIA method, which is patented as U.S. Pat. No. 5,720,296 to Cha. According to the U.S. patent, the body composition is measured by the steps of contacting a right palm, a right thumb, a left palm, a left thumb, a right front sole, a right rear sole, a left front sole and a left rear sole to eight electrodes, measuring segmental impedances by means of an impedance measuring instrument by selecting an electronic switch which is controlled by a micro-processor, measuring body weight by means of a weight measuring sensor, inputting body height, age and sex through a keyboard, and measuring an amount of body fluid (TBW), an amount of fat free mass (FFM), a percent body fat (%BF) and a distribution of body fluid (ECW/ICW), by means of the microprocessor. Although the U.S. patent has an advantage that the weight is automatically measured by a weight measuring sensor, it has still has a disadvantage that the measuring person inputs height, age, and sex through a keyboard. Such method gives inconvenience to the measuring persons who are not familiar with the operation of the apparatus.

In an attempt to overcome the above described disadvantage, the present inventor has developed a new apparatus for analyzing body composition and a method thereof, which is characterized by standing on the apparatus, gripping the hands bar of the apparatus, and adjusting the hands bar to the height of the measuring person.

OBJECTS OF THE INVENTION

Therefore, it is an object of the present invention to provide an apparatus for analyzing the body composition by measuring the bioelectrical impedance, in which the body composition can be analyzed in a simple and convenient manner even without inputting age and sex of the measuring person through a keyboard, like when measuring body weight on an electronic scale.

It is another object of the present invention to provide an apparatus for measuring the body composition, in which weight of the measuring person is measured by a measuring sensor and input to a microprocessor and in which height of the measuring person is input to the microprocessor by adjusting the hands bar.

It is still another object of the present invention an apparatus for measuring the body composition, in which the height is neither input through a keyboard nor measured in a direct way.

It is still another object of the present invention to provide an apparatus for measuring the body composition, which does not have a keyboard to input height, age, or sex of the measuring person.

The above objects and other advantages of the present invention can be achieved by the ensuing disclosure and appended claims.

SUMMARY OF THE INVENTION

In achieving the above objects, the apparatus for analyzing the body composition based on the bioelectrical impedance analysis according to the present invention includes a standing plate having four electrodes for contacting a right front sole, a right rear sole, a left front sole, and a left rear sole, respectively; a hands bar having four electrodes for contacting a right palm, a right thumb, a left palm, and a left thumb, respectively; a support rod for supporting the hands bar and connecting an axis; a display; a sensor for sensing the rotating position of the support rod and indicating the height of the measuring person to the display; an impedance measuring circuit for measuring the impedance based on a voltage-current ratio by making an alternating current flow between two of the electrodes and reading the voltage difference; an electronic switch for being controlled by a microprocessor to select electrical connections between the electrodes and the impedance measuring circuit; a weight measuring sensor for measuring the body weight of the measuring person; an A/D converter and amplifiers for interfacing the impedance measuring circuit, the weight measuring sensor, and the sensor for indicating the height to the micro-processor; and the microprocessor controlling the electronic switch and processing the data received from the impedance measuring circuit, the weight measuring sensor, and the sensor for indicating the height.

In the body composition analyzing apparatus of the present invention, the results processed by the microprocessor are displayed on the display, and when needed, a printer is added for printing the results.

The apparatus of this invention may be equipped with an interface for connecting an outside computer.

In another aspect of the present invention, the method for measuring the body impedance according to the present invention includes the steps of standing on the standing plate, thereby contacting a right front sole, a right rear sole, a left front sole, and a left rear sole on the four electrodes, respectively; gripping the hands bar, thereby contacting a right palm, a right thumb, a left palm, and a left thumb on the four electrodes, respectively; adjusting the hands bar to indicate the height of the measuring person; inputting the height to the microprocessor by the sensor for sensing the rotating position of the support rod; measuring segmental impedances by means of the impedance measuring circuit by the electronic switch which is controlled by the microprocessor; measuring body weight by means of the weight measuring sensor; and measuring an amount of body fluid (TBW), an amount of fat free mass (FFM), a percent body fat (%BF) and a distribution of body fluid (ECW/ICW), by means of the microprocessor.

The results of analysis can be displayed on a display unit or can be printed through a printer.

BRIEF DESCRIPTION OF THE DRAWINGS

The above objects and other advantages of the present invention will become more apparent by describing in detail the preferred embodiment of the present invention with reference to the attached drawings in which.

DETAILED DESCRIPTION OF THE PREFERRED EMBODIMENT

Figure 1:
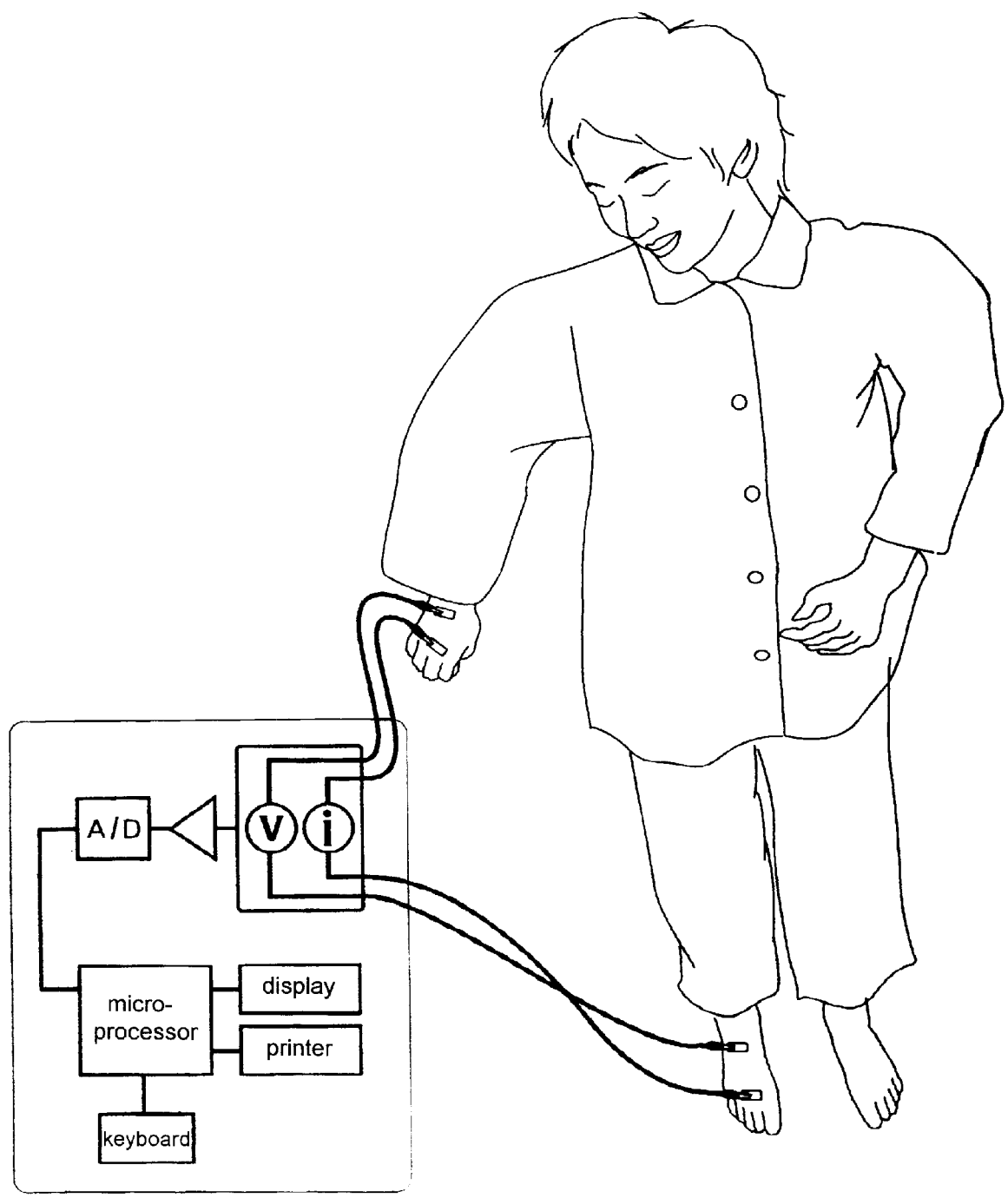
FIG. 1 is a schematic view showing a conventional embodiment using the BIA method.

FIG. 1 represents a conventional embodiment using the BIA method. According to the conventional BIA method, body composition is analyzed by a series of steps of attaching the electrodes on the hands and feet, inputting sex, age, weight, and height of the measuring person, measuring impedances at the respective body parts, calculating body compositions in a microprocessor, and displaying the resulting data on a display or printing the data out through a printer. Such conventional BIA method has disadvantages that an operator attaches the electrodes on the hands and feet of the measuring person, and that the operator or the measuring person inputs the sex, age, weight, and height of the measuring person through a keyboard.

Figure 2:
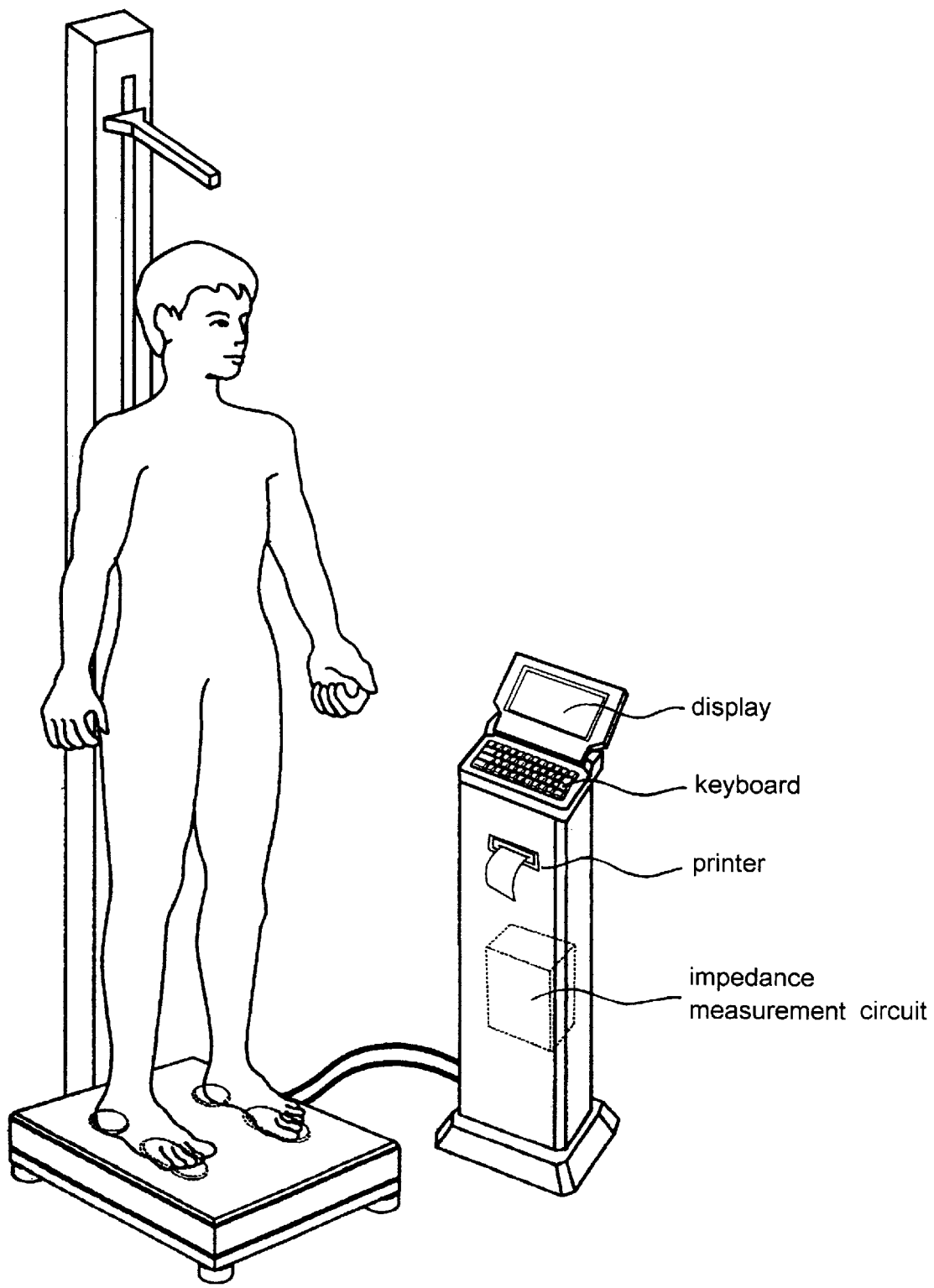
FIG. 2 is a schematic view showing another embodiment using the BIA method, which is patented as U.S. Pat. No. 5,720,296 to Cha.

FIG. 2 represents another embodiment using the BIA method, which is patented as U.S. Pat. No. 5,720,296 to Cha. According to the U.S. patent, the body composition is measured by the steps of contacting a right palm, a right thumb, a left palm, a left thumb, a right front sole, a right rear sole, a left front sole and a left rear sole to eight electrodes, measuring segmental impedances by means of an impedance measuring instrument by selecting an electronic switch which is controlled by a micro-processor, measuring body weight by means of a weight measuring sensor, inputting body height, age and sex through a keyboard, and measuring an amount of body fluid (TBW), an amount of fat free mass (FFM), a percent body fat (%BF) and a distribution of body fluid (ECW/ICW), by means of the microprocessor. Although the U.S. patent has an advantage that the weight is automatically measured by a weight measuring sensor, it has still has a disadvantage that the measuring person inputs height, age, and sex through a keyboard. Such method gives inconvenience to the measuring persons who are not familiar with the operation of the apparatus.

Figure 3A:
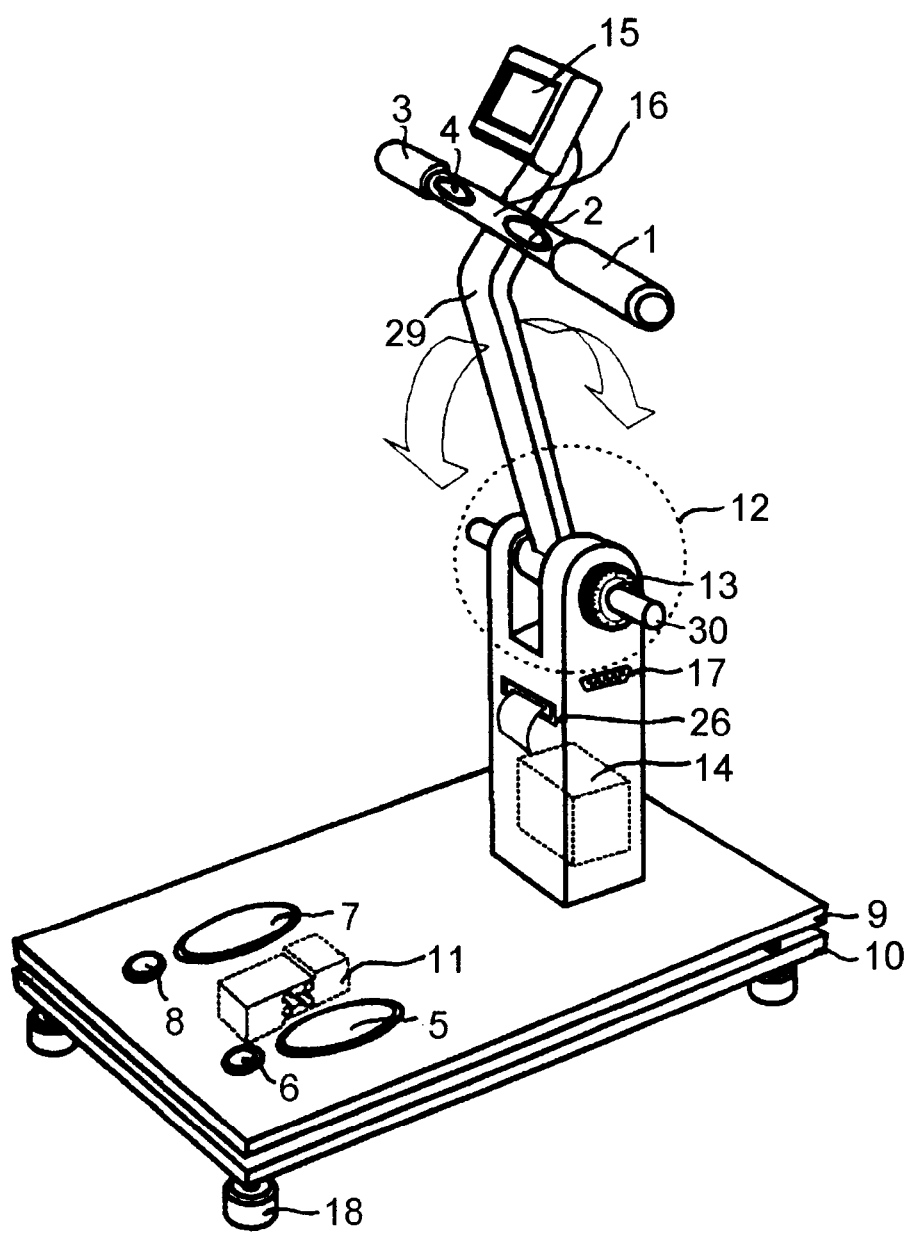
FIG. 3(a) illustrates a representative apparatus according to the present invention.
Figure 8:
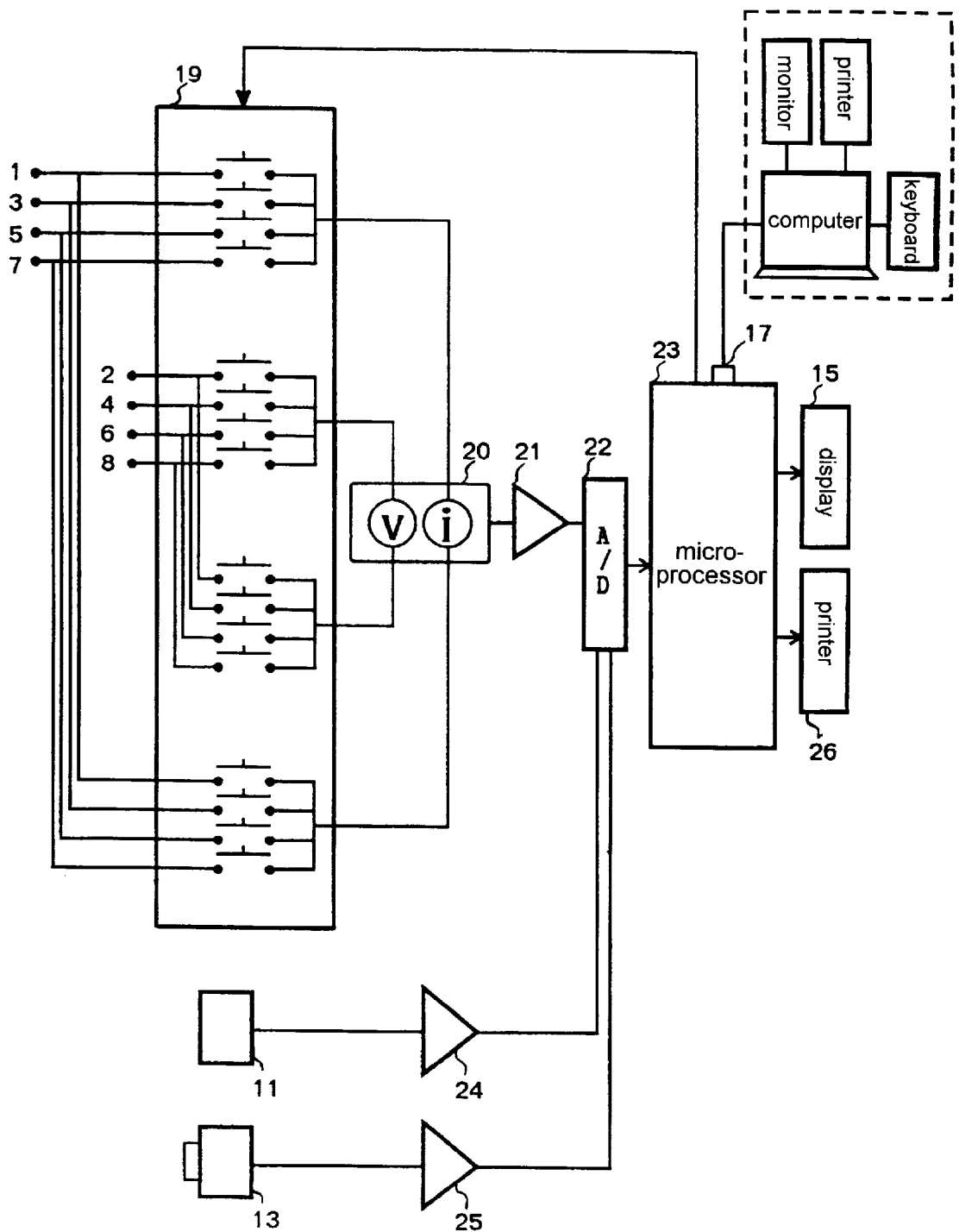
FIG. 8 illustrates the circuit of the body composition analyzing apparatus according to the present invention.

FIG. 3(a) illustrates a representative apparatus according to the present invention. FIG. 8 illustrates the circuit of the body composition analyzing apparatus according to the present invention. The circuit of FIG. 8 is shown as reference number 14 in FIG. 3(a). The apparatus of FIG. 3(a) includes a standing plate 9 having four electrodes 5, 6, 7 and 8 for contacting a right front sole, a right rear sole, a left front sole, and a left rear sole, respectively; a hands bar 16 having four electrodes 1, 2, 3 and 4 for contacting a right palm, a right thumb, a left palm, and a left thumb, respectively; a support rod 29 for supporting the hands bar and connecting an axis 30; a display 15; a sensor 13 for sensing the rotating position of the support rod and indicating the height of the measuring person to the display; an impedance measuring circuit 20 for measuring the impedance based on a voltage-current ratio by making an alternating current flow between two of the electrodes and reading the voltage difference; an electronic switch 19 for being controlled by a microprocessor 23 to select electrical connections between the electrodes 1–8 and the impedance measuring circuit; a weight measuring sensor 11 for measuring the body weight of the measuring person; an A/D converter 22 and amplifiers 21, 24 and 25 for interfacing the impedance measuring circuit, the weight measuring sensor, and the sensor for indicating the height to the micro-processor; and the microprocessor 23 controlling the electronic switch and processing the data received from the impedance measuring circuit, the weight measuring sensor, and the sensor for indicating the height.

When a measuring person stands on the standing plate 9, a right front sole, a right rear sole, a left front sole, and a left rear sole are contacted with electrodes 5, 6, 7 and 8, respectively. When the measuring person grip the hands bar 16, a right palm, a right thumb, a left palm, and a left thumb are contacted with four electrodes 1, 2, 3 and 4, respectively. The hands bar is jointed with a support rod 29 which is equipped with a display 15 at one end and which is connected with an axis 30. The hands bar, rod and display rotate backward and forward in one body at the axis 30. The rotating and sensing means 12 can be easily carried out to an ordinary skilled person in the art. A lower plate 10 is equipped under the standing plate 9, and rolls 18 are assembled with the lower plate downward.

The measuring person adjusts the hands bar by pulling or pushing it so as to indicate the height of the measuring person on the display 15. When the height is displayed in digital or in analog, the measuring person stops adjusting the hands bar for seconds, and the height is read by a sensor 13 and automatically inputted to the microprocessor 23. Segmental impedances are measured by means of the impedance measuring circuit 20 by the electronic switch 19 which is controlled by the microprocessor. Body weight is measured by means of the weight measuring sensor 11 and input to the microprocessor. An amount of body fluid (TBW), an amount of fat free mass (FFM), a percent body fat (%BF) and a distribution of body fluid (ECW/ICW) are analyzed by means of the microprocessor. The results of the analysis can be displayed on the display unit 15 or can be printed through a printer 26.

Figure 3B:
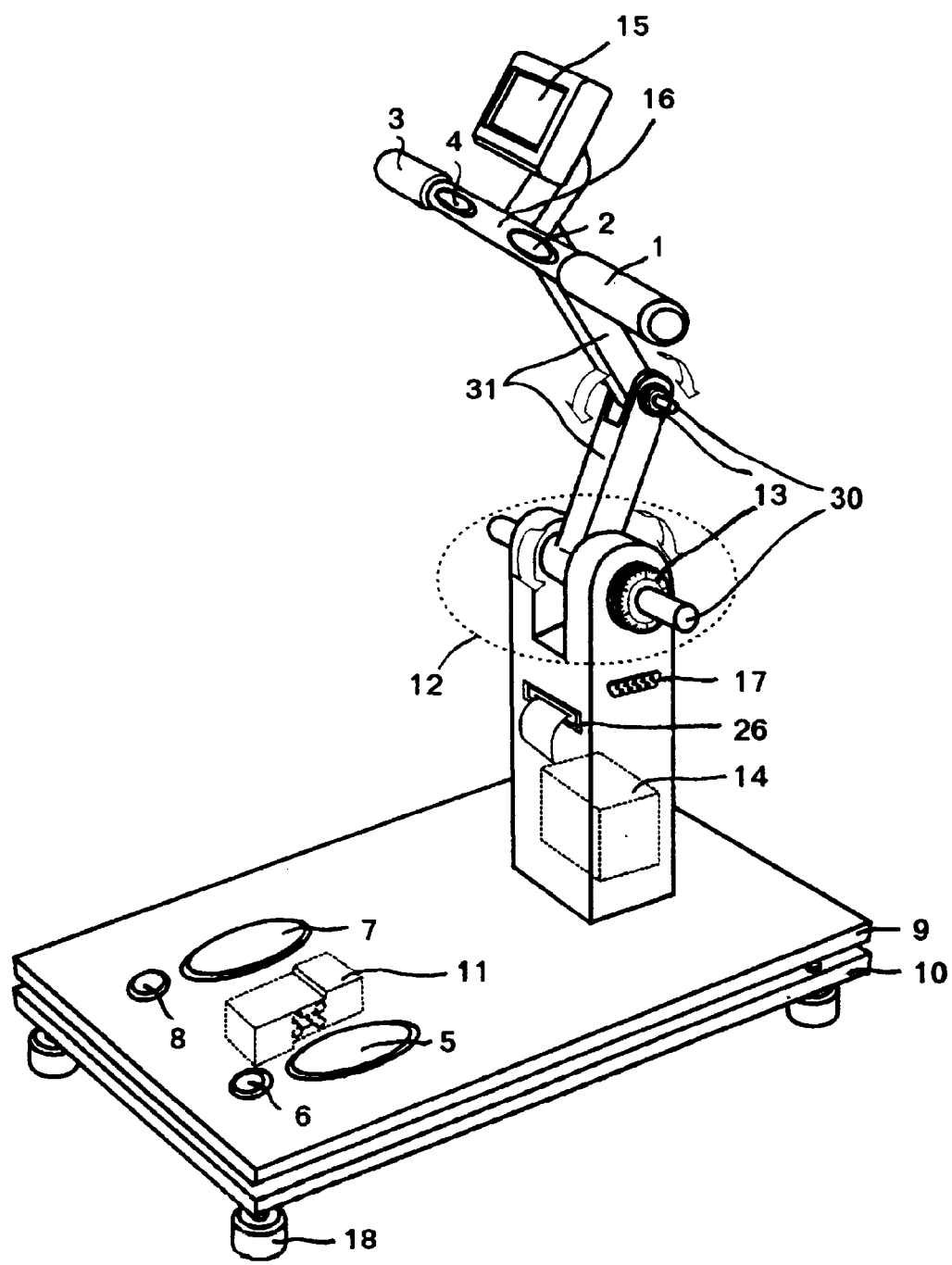
FIG. 3(b) illustrates another apparatus according to the present invention, having another axis for the rod 31 to rotate at two positions.

FIG. 3(b) illustrates another apparatus according to the present invention, having another axis for the rod 31 to rotate at two positions. In the embodiment of FIG. 3(b), the rod 31 is divided into two and has two axises 30. This embodiment is more convenient for a measuring person to use than that of FIG. 3(a). The two divided rod 31 is easily carried out by an ordinary skilled person in the art.

Figure 4A:
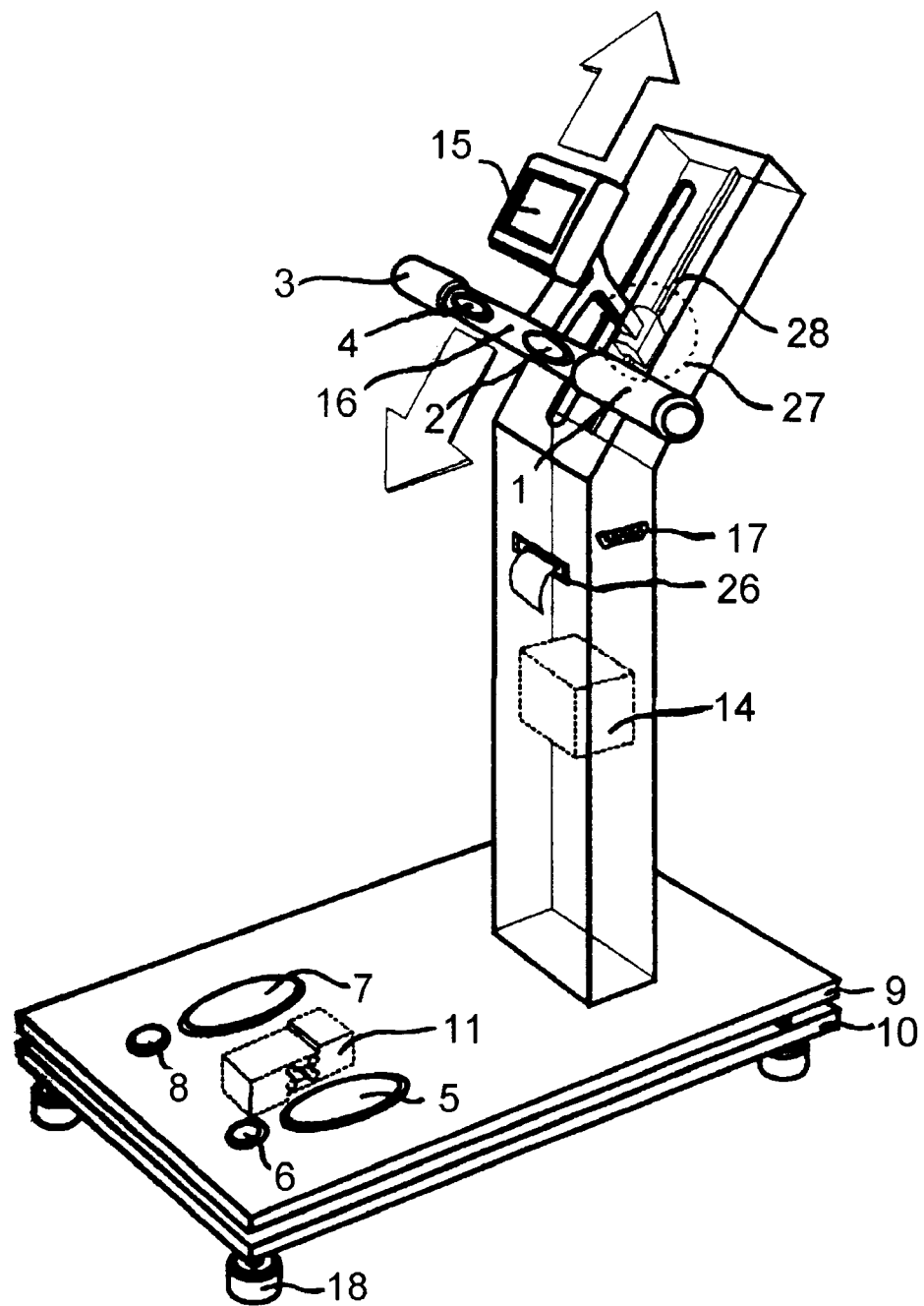
FIG. 4(a) illustrates another apparatus according to the present invention, which the hands bar and rod moves slidingly up and down.
Figure 4B:
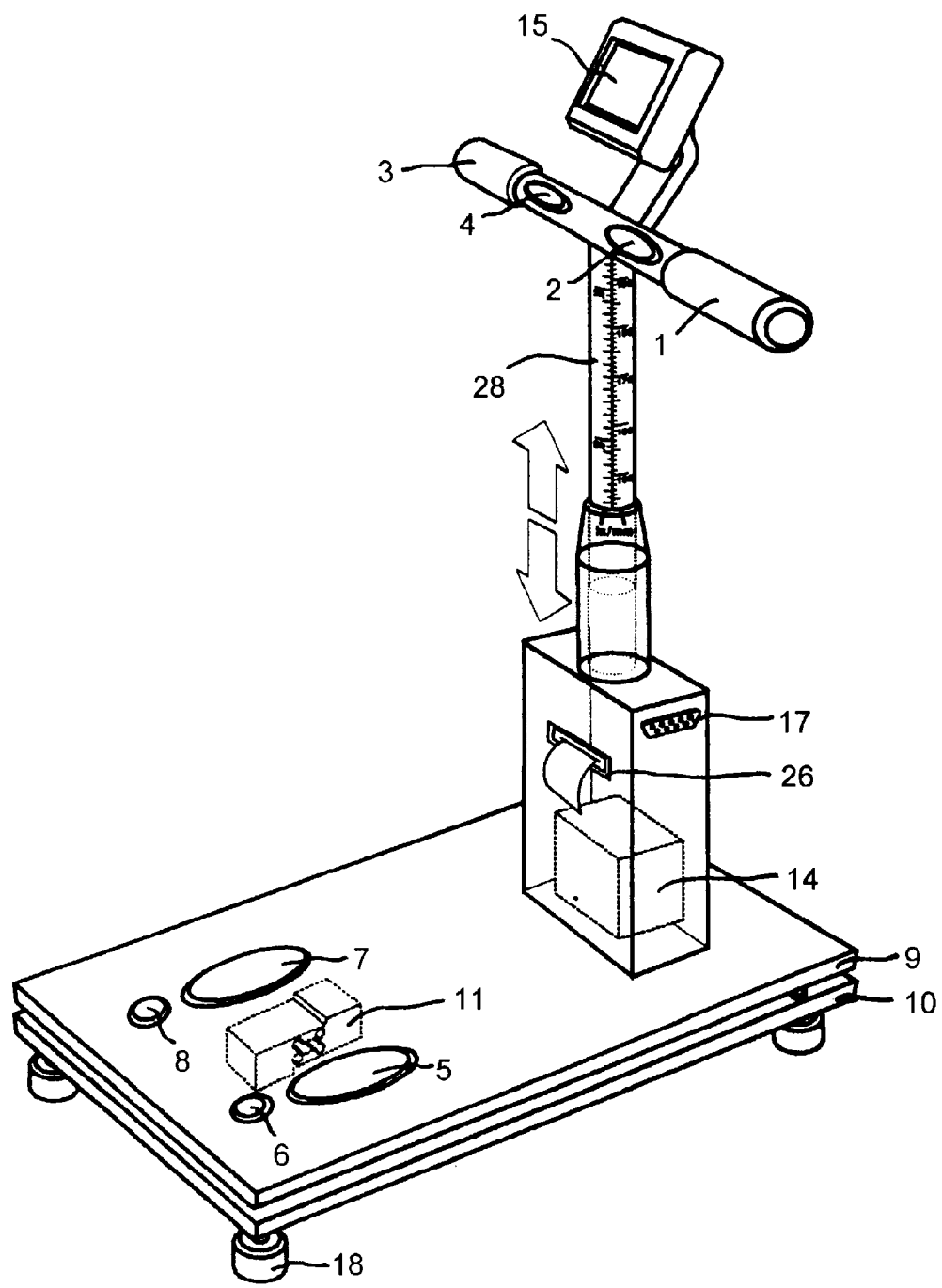
FIG. 4(b) illustrates another apparatus according to the present invention, which the hands bar and rod moves vertically up and down.

FIG. 4(a) illustrates another apparatus according to the present invention, which the hands bar and rod moves slidingly up and down, and FIG. 4(b) illustrates another apparatus according to the present invention, which the hands bar and rod moves vertically up and down. The apparatuses of FIGS. 4(a) and 4(b) do not have a keyboard thereon. Like in FIGS. 3(a) and 3(b), the height of a measuring person is indicated on the display 15 and input to the microprocessor. In FIG. 4(a), the adjusting means of the hands bar, display and rod moves slidingly up and down. In FIG. 4(b), the adjusting means moves vertically up and down. A vertical sensor 28 is installed in the support rod. The adjusting means of FIGS. 4(a) and 4(b) is easily carried out by an ordinary skilled person in the art.

Figure 5:
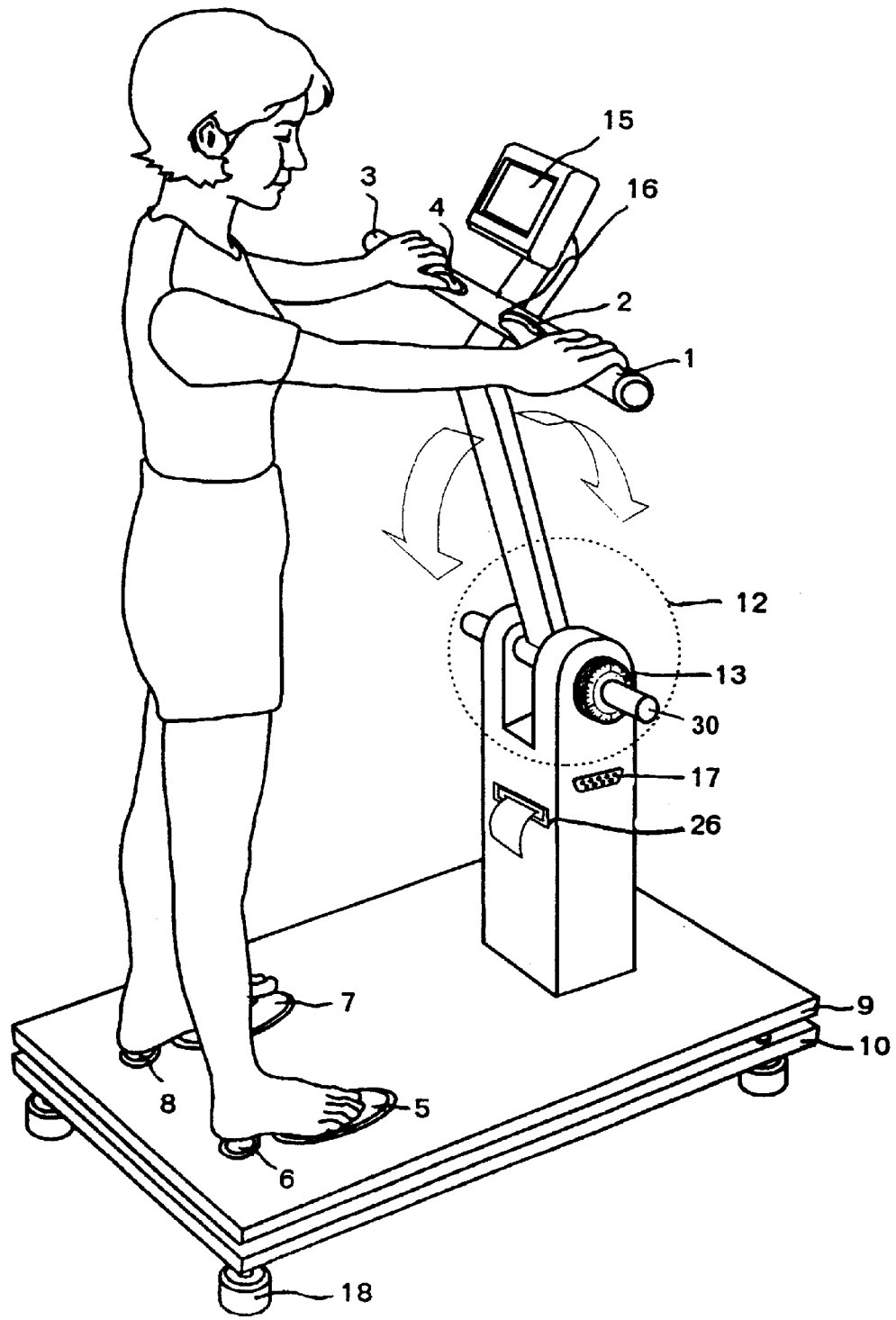
FIG. 5 is a schematic perspective view of using the apparatus of FIG. 3(a)

FIG. 5 is a schematic perspective view of using the apparatus of FIG. 3(a). A measuring person stands on the standing plate 9, thereby contacting a right front sole, a right rear sole, a left front sole, and a left rear sole on the four electrodes 5, 6, 7 and 8 respectively. The measuring person grips the hands bar 16 with both hands, thereby contacting a right palm, a right thumb, a left palm, and a left thumb on the four electrodes 1, 2, 3 and 4, respectively. The hands bar is adjusted to indicate the height of the measuring person by pulling or pushing it. When the height is displayed for seconds, the height is input to the microprocessor 23. Segmental impedances are measured by means of the impedance measuring circuit 20 by the electronic switch 19 which is controlled by the microprocessor. The method of measuring the segmental impedances is described in U.S. Pat. No. 5,720,296 to Cha. Body weight of the measuring person is input to the microprocessor by a weight measuring sensor 11. As a result of analyzing all the data above in accordance with a computer program, an amount of body fluid (TBW), an amount of fat free mass (FFM), a percent body fat (%BF) and a distribution of body fluid (ECW/ICW) are calculated. The results of analysis can be displayed on a display unit 15 or can be printed through a printer 26.

Figure 6A:
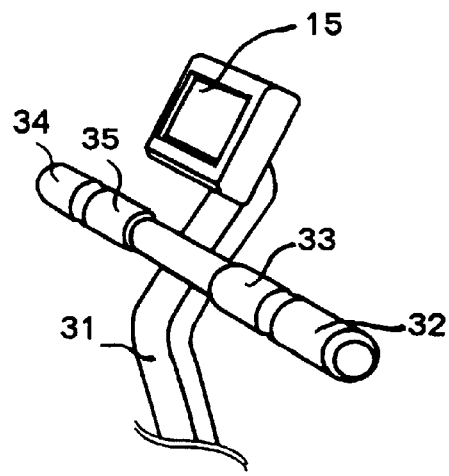
FIG. 6(a) is a perspective view of a modification of the hands bar.
Figure 6B:
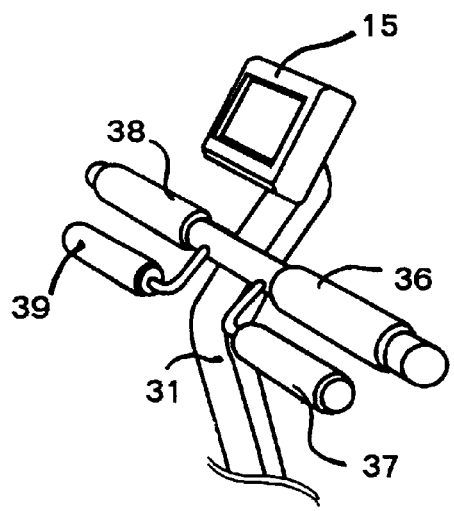
FIG. 6(b) is a perspective view of another modification of the hands bar.

FIG. 6(a) is a perspective view of a modification of the hands bar and FIG. 6(b) is a perspective view of another modification of the hands bar. The hands bar of FIG. 6(a) are formed with four electrodes 32, 33, 34 and 35 which will contact a right palm, a right thumb, a left palm, and a left thumb, respectively, when a measuring person grips the hands bar with both hands. The hands bar of FIG. 6(b) are formed with four electrodes 36, 37, 38 and 39 which will contact a right palm, a right thumb, a left palm, and a left thumb, respectively, when a measuring person grips the hands bar with both hands. The hands bars can be easily understood by an ordinary skilled person in the art.

Figure 7:
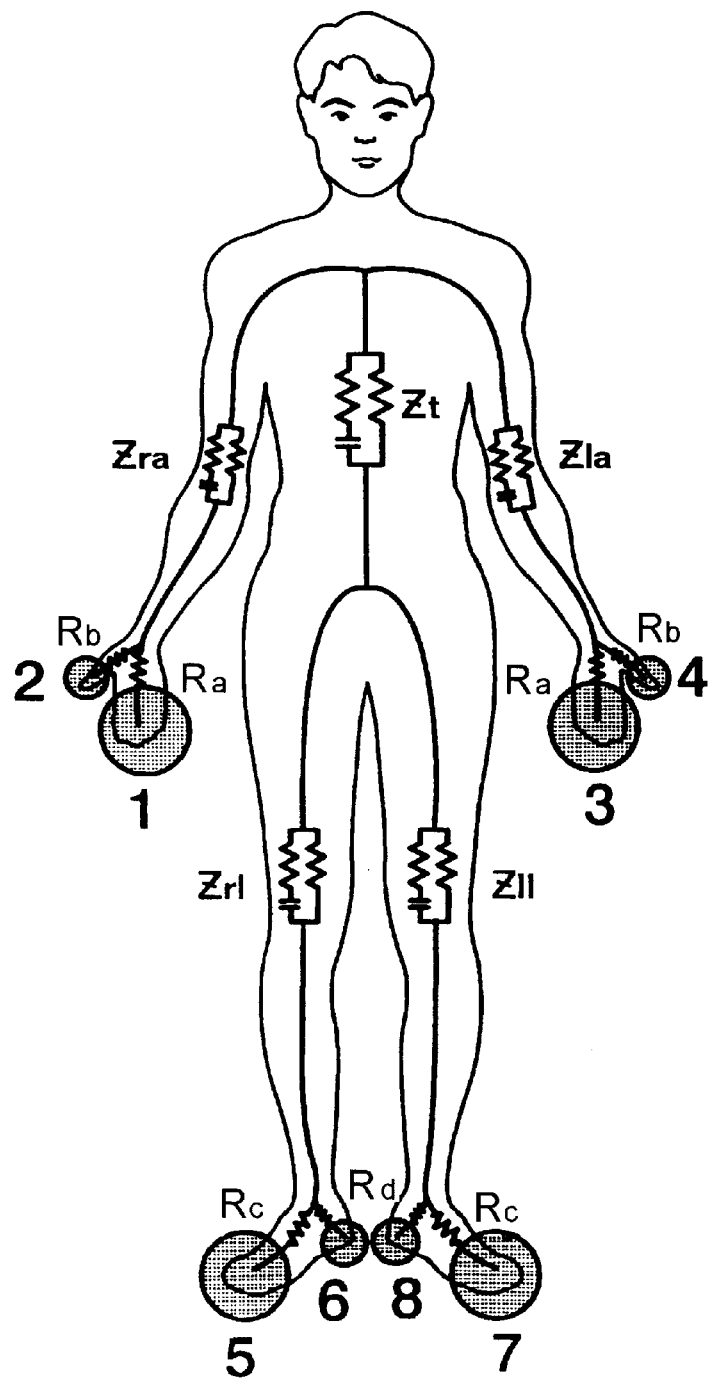
FIG. 7 schematically illustrates an impedance model of a human body to be measured by the apparatus according to the present invention.

FIG. 7 schematically illustrates an impedance model of a human body to be measured by the apparatus according to the present invention, and FIG. 8 illustrates the circuit of the body composition analyzing apparatus according to the present invention.

As shown in FIG. 7, the impedance from the right wrist to the joint of the right shoulder is indicated by $Z_{ra}$, the impedance from the left wrist to the joint of the left shoulder is indicated by $Z_{la}$, the impedance from the right ankle to the joint of the right hip joint is indicated by $Z_{rl}$, the impedance from the left ankle to the joint of the left hip joint is indicated by $Z_{ll}$, and the impedance of the trunk is indicated by $Z_t$. The resistance from the palm to the wrist is indicated by $R_a$, the resistance from the thumb to the wrist is indicated by $R_b$, the resistance from the front sole to the ankle is indicated by $R_c$, and the resistance from the rear sole to the ankle is indicated by $R_d$. However, the resistances $R_a$, $R_b$, $R_c$, and $R_d$ do not affect the impedances very much.

The microprocessor 23 controls the electronic switch 19 to select electrical connections between the electrodes 1–8 and the impedance measuring circuit 20.

The electronic switch 19 is connected between electrodes 1 and 5 by a command of the micro-processor 23, so that an electric current would flow between the electrodes 1 and 5. Further, the electronic switch 10 is connected between electrodes 2 and 4 by a command of the micro-processor, so that the voltage between the electrodes 2 and 4 can be measured. Thus the impedance $Z_{ra}$ can be obtained from the above mentioned current and voltage.

The electronic switch 19 is connected between electrodes 1 and 5 by a command of the micro-processor 23, so that an electric current would flow between the electrodes 1 and 5. Further, the electronic switch 10 is connected between electrodes 4 and 8 by a command of the micro-processor, so that the voltage between the electrodes 4 and 8 can be measured. Thus the impedance $Z_t$ can be obtained from the above mentioned current and voltage.

The electronic switch 19 is connected between electrodes 1 and 5 by a command of the micro-processor 23, so that an electric current would flow between the electrodes 1 and 5. Further, the electronic switch 10 is connected between electrodes 6 and 8 by a command of the micro-processor, so that the voltage between the electrodes 6 and 8 can be measured. Thus the impedance $Z_{rl}$, can be obtained from the above mentioned current and voltage.

The electronic switch 19 is connected between electrodes 3 and 7 by a command of the micro-processor 23, so that an electric current would flow between the electrodes 3 and 7. Further, the electronic switch 10 is connected between electrodes 2 and 4 by a command of the micro-processor, so that the voltage between the electrodes 2 and 4 can be measured. Thus the impedance $Z_{la}$, can be obtained from the above mentioned current and voltage.

The electronic switch 19 is connected between electrodes 3 and 7 by a command of the micro-processor 23, so that an electric current would flow between the electrodes 3 and 7. Further, the electronic switch 10 is connected between electrodes 6 and 8 by a command of the micro-processor, so that the voltage between the electrodes 6 and 8 can be measured. Thus the impedance $Z_{ll}$, can be obtained from the above mentioned current and voltage.

To obtain the impedances $Z_{ra}$, $Z_t$, $Z_{rl}$, $Z_{la}$ and $Z_{ll}$, the voltage electrodes are switched to current electrodes, and vise versa, which will be conducted by the electronic switch 19. For example, if the electrode 1 is a current electrode, then the electrode 2 is a voltage electrode, while if the electrode 2 is a current electrode, the electrode 1 is a voltage electrode. The electrodes 3 and 4 are also used in such a manner that they should serve different functions, and the electrodes 5 and 6 are also used in the same manner, while the electrodes 7 and 8 are also used in the same manner. That is, each of the electrodes 1–8 serves as a current electrode or a voltage electrode. If the electrodes 1, 3, 5 and 7 are used as current electrodes, then the electrodes 2, 4, 6 and 8 are used as voltage electrodes. On the other hand, if the electrodes 2, 4, 6 and 8 are used as current electrodes, then the electrodes 1, 3, 5 and 7 are used as voltage electrodes. In measuring the impedances of the different body segments, the electrical connections between the electrodes 1–8 and the impedance measuring circuit 20 are switched many times based on the segmental measurement. In order to automatize this, there is the electronic switch 19 which is opened/closed by the microprocessor 23. The impedances $Z_{ra}$, $Z_t$, $Z_{rl}$, and $Z_{ll}$ are input to the microprocessor 23.

The height of a measuring person is sensed by a sensor 13, amplified by an amplifier 25, and input to the microprocessor.

The body weight of a measuring person is measured by a weight measuring sensor 11 which is installed under the standing plate 9. The measured body weight is transferred through the amplifier 24 and the A/D converter 22 to the microprocessor 23. The impedance values which are measured by the impedance measuring circuit 20 also are transferred through the amplifier 21 and the A/D converter 2 to the microprocessor 23.

Based on the impedances, body height, and weight which are stored in the microprocessor, the body composition such as the amount of the body fluid (TBW), the fat free mass (FFM), the body fat proportion(% BF), and the body fluid distribution ratio inside and outside the cells are analyzed. The analyzed results are displayed on the display unit 15, and printed by the printer 26.

The apparatus of this invention may be equipped with an interface 17 for connecting an outside computer for further calculation and storage of the data.

Examples for computing the body composition from the measured impedances are as follows. It is assumed that the left and right arms and legs and the trunk are five cylindrical conductors which have uniform cross sectional areas and which are similar in length. Based on this assumption, the segmental impedances are measured.

The total body water (TBW) is the sum of the segmental water, and is defined as follows:

$$\text{TBW} = C_1(Ht^2/Z_{ra} + Ht^2/Z_{la}) + C_2 Ht^2/Z_t + C_3(Ht^2/Z_{ra} + Ht^2/Z_{la}) \quad (I)$$

wherein $C_1$, $C_2$, and $C_3$ are the best suitable constants, and Ht is the height of the measuring person.

Equation (I) is stored in the microprocessor, and therefore, TBW can be obtained from the measured impedances and the height.

Body fat contains relatively small amount of water, and therefore, this water content is disregarded. The fat free mass (FFM) contains about 73% of water, and therefore, FFM is defined as follow:

$$\text{FFM} = \text{TBW}/0.73 \quad (II)$$

The amount of body fat (FAT) is defined to be the weight (Wt) minus FEM, and is defined by Equation (III), thus percent body fat (% BF) is defined by Equation (IV) as follow:

$$\text{FAT} = Wt - \text{FFM} \quad (III)$$

$$\% \text{ BF} = (Wt - \text{FFM}) \times 100/Wt \quad (IV)$$

Further, in this invention, a segmental water of a human body can be obtained in accordance with a programmed equation. For example, the segmental water of right arm ($SW_{ra}$) is represented as follow:

$$SW_{ra} = f(Ht, Wt, Z_{hra}, Z_{lra}) \quad (V)$$

wherein Ht is height, Wt is weight, $Z_{hra}$ is impedance of right arm measured at a high frequency, and $Z_{lra}$ is impedance of right arm measured at a low frequency.

Similarly, the segmental water of left arm ($SW_{la}$), segmental water of trunk ($SW_t$), segmental water of right leg ($SW_{rl}$), and segmental water of left leg ($SW_{ll}$) are represented as follow:

$$SW_{la} = f(Ht, Wt, Z_{hla}, Z_{lla}) \quad (VI)$$

$$SW_t = f(Ht, Wt, Z_{ht}, Z_{lt}) \quad (VII)$$

$$SW_{lr} = f(Ht, Wt, Z_{hrl}, Z_{lrl}) \quad (VIII)$$

$$SW_{ll} = f(Ht, Wt, Z_{hll}, Z_{lll}) \quad (IX)$$

wherein Ht is height, Wt is weight, $Z_{hla}$ is impedance of left arm measured at a high frequency, $Z_{lra}$ is impedance of right arm measured at a low frequency, $Z_{ht}$ is impedance of trunk measured at a high frequency, $Z_{lt}$ is impedance of trunk measured at a low frequency, $Z_{hrl}$ is impedance of right leg measured at a high frequency, and $Z_{lll}$ is impedance of left leg measured at a low frequency.

The results of analysis can be displayed on a display unit 15 or can be printed through a printer 26.

According to the present invention as described above, even without assistance of a specially trained person, the measuring person can stand with the two legs on the electrodes, and can grasp the electrode rods with two hands, so that the right palm, the right thumb, the left palm, the left thumb, the right front sole, the right rear sole, the left front sole and the left rear sole would be contacted with eight different electrodes. Thus the impedances of the different body portions are automatically measured by the eight electrodes, and the body composition is analyzed in a convenient and simple manner.

It should be apparent to those skilled in the art that various changes and modifications can be added to the present invention without departing from the scope of the present invention which is limited only by the appended claims.

What is claimed is:

1. An apparatus for analyzing the body composition of a person based on bioelectrical impedance analysis, which comprises:

a standing plate having four electrodes for contacting a right front sole, a right rear sole, a left front sole, and a left rear sole, respectively;

a hands bar having four electrodes for contacting a right palm, a right thumb, a left palm, and a left thumb, respectively;

a support rod for supporting the hands bar, the support rod being connected to an axis to permit rotation;

a display attached to the support rod;

a sensor for sensing the rotating position of the support rod and the height of the person to the display;

an impedance measuring circuit for measuring the impedance based on a voltage-current ratio by making an alternating current flow between a pair of electrodes and reading the voltage difference;

an electronic switch for being controlled by a microprocessor to select electrical connections between the eight electrodes and the impedance measuring circuit;

a weight measuring sensor; and an A/D converter and amplifiers for interfacing the impedance measuring circuit, the weight measuring sensor, and the sensor for indicating the height to the microprocessor, wherein the microprocessor controls the electronic switch and processing data received from the impedance measuring circuit, the weight measuring sensor, and the sensor for indicating the height.

2. The apparatus as claimed in claim 1, wherein said support rod is divided into two and has two axes.

3. The apparatus as claimed in claim 1, further comprising an interface for connecting an outside computer for further calculation and storage of the data.

4. The apparatus as claimed in claim 1, further comprising a printer for printing the results of analysis body composition.

5. The apparatus as claimed in claim 1, wherein voltage electrodes can be switched to current electrodes and current electrodes can be switched to voltage electrodes.

6. The apparatus as claimed in claim 1, wherein said hands bar and rod moves slidingly up and down, and a vertical sensor is installed in the support rod.

7. The apparatus as claimed in claim 1, wherein said hands bar and rod moves vertically up and down, and a vertical sensor is installed in the support rod.

8. The apparatus as claimed in claim 1, wherein the electrodes on the hands bar are formed to contact a right palm, a right thumb, a left palm, and a left thumb when a measuring person grips the hands bar with both hands.

9. A method for measuring the body composition of a person, which comprises:

standing on the standing plate, thereby contacting a right front sole, a right rear sole, a left front sole, and a left rear sole on the four electrodes, respectively;

gripping the hands bar, thereby contacting a right palm, a right thumb, a left palm, and a left thumb on the four electrodes, respectively;

adjusting the hands bar to indicate the height of the person;

inputting the height to a microprocessor by a sensor for sensing the rotating position of a support rod;

measuring segmental impedances by means of the impedance measuring circuit by the electronic switch which is controlled by the microprocessor;

measuring body weight of the person by means of a weight measuring sensor; and measuring an amount of body fluid (TBW), an amount of fat free mass (FFM), a percent body fat (%BF) and a distribution of body fluid (ECW/ICW), by means of the microprocessor.

10. The method as claimed in claim 9, further comprising a step of connecting an outside computer through an interface for further calculation and storage of the data.

11. The method as claimed in claim 9, further comprising a step of printing the results of analysis body composition.

* * * * *